United States Patent
Cobanoglu et al.

(10) Patent No.: US 11,179,103 B2
(45) Date of Patent: Nov. 23, 2021

(54) WEARABLE STEP COUNTER SYSTEM

(71) Applicant: Sanko Tekstil Isletmeleri San. Ve Tic. A.S., Inegol-Bursa (TR)

(72) Inventors: Ozgur Cobanoglu, Inegol-Bursa (TR); Fehim Caglar, Inegol-Bursa (TR); Ali Kemal Agirman, Inegol-Bursa (TR); Jitka Eryilmaz, Inegol-Bursa (TR)

(73) Assignee: Sanko Tekstil Isletmeleri San. Ve Tic. A.S., Inegol-Bursa (TR)

( * ) Notice: Subject to any disclaimer, the term of this patent is extended or adjusted under 35 U.S.C. 154(b) by 255 days.

(21) Appl. No.: 15/497,596

(22) Filed: Apr. 26, 2017

(65) Prior Publication Data

US 2017/0311889 A1    Nov. 2, 2017

(30) Foreign Application Priority Data

Apr. 29, 2016    (EP) ...................................... 16167598

(51) Int. Cl.
*A61B 5/00* (2006.01)
*A61B 5/11* (2006.01)
(Continued)

(52) U.S. Cl.
CPC .............. *A61B 5/6804* (2013.01); *A61B 5/11* (2013.01); *A61B 5/1118* (2013.01); *D02G 3/441* (2013.01);
(Continued)

(58) Field of Classification Search
CPC ......... A61B 5/6804; A61B 5/11; A61B 5/112; A61B 5/6829; A61B 2562/006;
(Continued)

(56) References Cited

U.S. PATENT DOCUMENTS

| 6,324,053 B1* | 11/2001 | Kamijo | ................... G06F 1/163 |
| | | | 2/264 |
| 2003/0212319 A1* | 11/2003 | Magill | ................. A61B 5/0408 |
| | | | 600/382 |

(Continued)

FOREIGN PATENT DOCUMENTS

| CN | 102300499 | 12/2011 |
| EP | 2578141 | 4/2013 |

(Continued)

OTHER PUBLICATIONS

Haescher, Marian, CapWalk: a capacitive recognition of walking-based activities as a wearable assistive technology, Jul. 2015, PETRA, Article No. 35, pp. 1-8 (Year: 2015).*

(Continued)

*Primary Examiner* — Linda C Dvorak
*Assistant Examiner* — Annabeth E Rodriguez
(74) *Attorney, Agent, or Firm* — Silvia Salvadori

(57) ABSTRACT

Disclosed is a wearable step counter system comprising a garment for a wearer's legs, a capacitive electrode and a microcontroller, said garment comprising a textile fabric portion, said capacitive electrode comprising an electrically conductive yarn woven into said textile fabric portion, said textile fabric portion being arranged on said garment for providing a parasitic capacitive coupling between said capacitive electrode and a wearer's leg, said microcontroller being electrically connected to said capacitive electrode for evaluating said parasitic capacitive coupling so that the relative movement between the wearer's legs is detected by the microcontroller.

25 Claims, 10 Drawing Sheets

(51) Int. Cl.
  *D03D 1/00* (2006.01)
  *G01C 22/00* (2006.01)
  *D02G 3/44* (2006.01)
  *A41D 1/06* (2006.01)
  *A41D 1/00* (2018.01)

(52) U.S. Cl.
  CPC ......... *D03D 1/0088* (2013.01); *G01C 22/006* (2013.01); *A41D 1/005* (2013.01); *A41D 1/06* (2013.01); *A61B 5/112* (2013.01); *D10B 2101/20* (2013.01); *D10B 2201/02* (2013.01); *D10B 2401/18* (2013.01)

(58) Field of Classification Search
  CPC .......... A61B 5/6805; A61B 2562/0214; A41D 1/06; D03D 1/0088; G01C 22/066; A61N 1/36003; A61N 1/3614; A61N 1/36135
  See application file for complete search history.

(56) References Cited

U.S. PATENT DOCUMENTS

| | | | |
|---|---|---|---|
| 2008/0196783 A1* | 8/2008 | Van Bruggen | D03D 1/0088 139/319 |
| 2011/0015498 A1* | 1/2011 | Mestrovic | A61B 5/01 600/301 |
| 2013/0066168 A1 | 3/2013 | Chang-Ming et al. | |
| 2013/0211208 A1* | 8/2013 | Varadan | A61B 5/14552 600/301 |
| 2014/0343392 A1* | 11/2014 | Yang | A61B 5/04082 600/393 |
| 2015/0250420 A1* | 9/2015 | Longinotti-Buitoni | A61B 5/6804 600/301 |
| 2016/0290878 A1* | 10/2016 | Severinkangas | G01L 1/146 |

FOREIGN PATENT DOCUMENTS

| | | |
|---|---|---|
| EP | 2591717 | 5/2013 |
| JP | 2013-534833 | 9/2013 |
| JP | 2016-509635 | 3/2016 |
| WO | 2014093888 | 6/2014 |
| WO | 2016025554 | 8/2015 |

OTHER PUBLICATIONS

International Preliminary Report on Patentability dated Nov. 8, 2018 for corresponding International application No. PCT/EP2017/059947.
European Search report dated Nov. 7, 2016 for Priority European application No. 16167598.8.
International Search Report of PCT/EP2017/059947 dated Jul. 31, 2017.
Jingyuan Cheng et al., "Designing sensitive wearable capacitive sensors for activity recognition" IEEE Sensors Journal, vol. 13 No. 10, Oct. 2013.
Marian Haescher et al. "CapWalk" pervasive technologies related to assistive environments, acm, 2 penn plaza, suite 701 new York 10121-0701 USA, Jul. 1, 2015.
Matthias Kreil et al., "Muscle Activity Evaluation using Force Sensitive Resistors" Medical Devices and Biosensors, 2008, 5th International Summer School and Symposium Jun. 1-3, 2008.
Jingyuan Cheng et al., "Active capacitive sensing: exploring a new wearable sensing modality for activity recognition" May 17, 2010, Pervasive Computing, Spriger Berlin Heidelberg.
Office Action issued by the CN patent office for corresponding patent application No. 201710301811.9 dated Dec. 26, 2019 and relevant letter form the CN Local Agent.
Office Action issued by the CN patent office for corresponding patent application No. 201710301811.9 dated Oct. 13, 2020 and relevant letter from the CN Local Agent.
Office Action dated Feb. 9, 2021 by the Japanese Patent Office for corresponding JP patent application No. 2017-089420 and relevat local agent's letter.

* cited by examiner

WEARABLE STEP COUNTER SYSTEM

RELATED APPLICATIONS

This application is related to, and claims priority to, European application EP 16167598.8, filed on 29 Apr. 2016 and entitled "Wearable step counter system", the contents of which are hereby incorporated by reference, as if set forth in their entirety.

FIELD OF THE INVENTION

The present invention relates to the field of devices for measuring physical activity of a user. More particularly, the present invention relates to a wearable step counter system, a method for detecting the number of steps taken by a user, and a method for producing a wearable step counter system.

BACKGROUND

Step counters are usually used for counting the steps taken by a user, e.g. for determining the distance walked by the user during a physical activity. Typically, step counters detect the movements of the user by means of bulky accelerometers located preferably on a belt, an arm or a wrist of the user. As a result, movement of these parts of the body can be interpreted as a walking or running activity. Traditional step counters have the problem of indicating a false count of steps in some circumstances, for example when a user is driving a car, or in general when the user is subjected to acceleration without carrying out any physical activity.

For solving this problem, some step counter systems comprise electromyography (EMG) sensors arranged on the user's legs, for detecting the activity of the leg muscles. In this way, user's steps can be detected independently from the acceleration of the user. Another solution provides to use strain gauges located on shoe soles under the user's feet for detecting the user's weight.

These solutions however have some drawbacks. EMG sensors require at least three electrodes for each leg, and are uncomfortable to be worn by the user because electrodes must be in contact with the skin of the user. Strain gauges require complex materials to function properly. Furthermore, the location under the user's feet makes the acquisition of the signals very difficult. In both cases, the above approaches can be expensive and uncomfortable for daily use by a user.

SUMMARY

The present invention overcomes drawbacks of the prior art approaches cited above and provides a step counter system and a method for detecting a number of steps of a user that are able to detect with accuracy the steps carried out by the user, i.e. the number of steps taken by a user, in a reliable manner without losing physical comfort and stylish appearance.

A further object of the present invention is to provide a method for producing a wearable step counter system that is easily assembled onto a garment without losing physical comfort and stylish appearance.

A further object of the present invention is to provide a wearable step counter system able to detect different types of gait styles. In various embodiments, the wearable step counter forms a portion of the fabric of the garment, e.g. an electrically conductive yarn is woven into a textile fabric portion and forms part of the garment.

These and other objects are reached by the present invention by means of a wearable step counter system, a method for detecting the number of steps of a user, and a method for producing a wearable step counter according to the claims.

Disclosed is a wearable step counter system that includes a garment for a wearer's legs, a capacitive electrode and a microcontroller.

The term "garment for a wearer's legs" is meant to indicate a garment intended to cover at least partially one or both legs of a user, such as pants, sport pants, shorts, socks, tights, leg warmers, and the like.

In various embodiments, the garment includes a textile fabric portion, the capacitive electrode comprising an electrically conductive yarn woven into the textile fabric portion. The textile fabric portion is arranged on the garment for providing a parasitic capacitive coupling between the capacitive electrode and a wearer's leg. The microcontroller is electrically connected to the capacitive electrode for evaluating the parasitic capacitive coupling so that the relative movement between the wearer's legs is detected by the microcontroller.

The term "parasitic capacitive coupling" is meant to indicate the capacitive coupling between the capacitive electrode and the parasitic capacitance of the wearer's leg. In general, when an object capable of providing parasitic capacitance (e.g. a wearer's leg) approaches the capacitive electrode of the step counter system according the present invention, an increase of the capacitance occurs in the capacitive electrode. This fact is due to the capacitive coupling between the capacitive electrode and the parasitic capacitance of the object approaching the capacitive electrode. In other words the capacitive electrode of the system according the present invention works as a sort of capacitive sensor for sensing the proximity of a user's leg with respect to the other.

As a result of embodiments of the present invention, the wearable step counter system can be integrated on a garment in a simple manner without losing physical comfort and stylish appearance. Furthermore, the wearable step counter system of the invention can be produced economically with all types of garments for a wearer's legs.

According to aspects of the present invention, the microcontroller is configured to evaluate parasitic capacitive coupling by detecting a capacitance value of the capacitive electrode.

Some embodiments provide the microcontroller configured to evaluate the distance and/or the cross-sectional overlap between the wearer's legs on the basis of the parasitic capacitive coupling.

In accordance with this aspect, the distance between the wearer's legs can be detected independently from the acceleration to which the user can be subjected (e.g. when the user is driving a car or in general when the user is not carrying out a physical activity).

According to another embodiment, the microcontroller is configured to evaluate the capacitance value of the capacitive electrode as a function of time. In this manner, the step counter system is able to accurately detect the steps carried out by the user in a reliable manner.

According to other embodiments, the capacitive electrode is arranged substantially along the full length of the garment.

This aspect allows for the detection of different types of gait styles with accuracy and reliability, but in other embodiments, the capacitive electrode is arranged along only a portion of the garment.

According to some embodiments, the electrically conductive yarn comprises an electrically conductive core and an electrically insulating external surface. Some embodiments of the present invention provide that the conductive core is made of a material chosen from steel, copper, silver and a conductive polymer.

Some embodiments of the present invention provide that the electrically insulating external surface is made of a material chosen from cotton, polyester, polyurethane and polypropylene.

Advantageously, the textile fabric portion comprises a set, i.e., group, of non-isolated conductive yarns interlacing the electrically conductive yarn, the set of non-isolated conductive yarns being arranged to provide an electrical grounding grid, the electrical grounding grid being arranged for touching the wearer's skin.

Some embodiments of the present invention provide that the non-isolated conductive yarns are made of steel or of steel twisted around cotton or of a steel-cotton blend.

According to various embodiments, the garment is a two-legged garment comprising a first garment leg and a second garment leg, the textile fabric portion being arranged on the first garment leg.

Some embodiments of the present invention provide that the textile fabric portion comprises a first textile fabric portion arranged on the first garment leg and a second textile fabric portion arranged on the second garment leg. The step counter system comprises first and second capacitive electrodes, the electrically conductive yarn of the first capacitive electrode being woven into said first textile fabric portion, the electrically conductive yarn of the second capacitive electrode being woven into the second textile fabric portion.

As a result of this aspect, the sensibility of the parasitic capacitive coupling is improved, for example by summing the capacitance values detected from the first capacitive electrode with the capacitance values detected from the second capacitive electrode.

According to a further aspect, the wearable step counter system comprises a matching electrode arranged on the second garment leg, the matching electrode comprising an electrically conductive yarn connected to ground. As a result of this aspect, the capacitance values of the capacitive electrode can be detected with respect to the ground with accuracy and reliability.

Advantageously, the matching electrode is arranged substantially along the full length of said garment.

According to a further aspect, the disclosure provides a wearable step counter system that comprises the electrically conductive yarn woven into the garment together with a coating that serves as a capacitive sensor. The coating may be a flexible (co)polymer matrix with dispersed conductive impurities formed using a variety of different materials.

In some advantageous embodiments, the garment is a pair of pants. The wearable step counter can be used not only for monitoring a physical activity of the wearer, but in general for monitoring the general health status of the wearer. For example, the wearable step counter can be used for monitoring the stress level, or the position of the legs of a user during a sedentary working activity, etc.

The present invention further relates to a method for detecting a number of steps of a user, the method comprising:
  i. providing a garment for a wearer's legs, the garment including a capacitive electrode and a microcontroller coupled thereto, the garment including a textile fabric portion with electrically conductive yarn woven into the textile fabric portion and forming part of a first leg of the garment, the electrically conductive yarn forming the capacitive electrode, and
  ii. detecting parasitic capacitance between the capacitive electrode and the second leg of said garment.

In some embodiments, the detecting comprises detecting the parasitic capacitance at a plurality of locations along said second leg.

In some embodiments, the method further comprising converting the parasitic capacitance to distance between the capacitive electrode on said first leg, and the wearer's leg disposed in the second leg of said garment.

In some embodiments, the detecting comprises detecting at least periodically over a period of time, and further comprising calculating a number of steps taken by wearer based on the detecting at least periodically over a period of time.

The present invention further relates to a method for producing a wearable step counter system comprising the steps of:
  a) providing a garment for a wearer's legs, wherein the garment comprises a textile fabric portion;
  b) weaving an electrically conductive yarn into the textile fabric portion of the garment for providing a capacitive electrode;
  c) providing a microcontroller electrically connected to the capacitive electrode for evaluating the parasitic capacitive coupling between the capacitive electrode and a wearer's leg, so that the relative movement between the wearer's legs is detected by the microcontroller.

BRIEF DESCRIPTION OF THE DRAWINGS

Further aspects and advantages of the present invention will be discussed more in detail with reference to the enclosed drawings, given by way of non-limiting example, wherein.

DETAILED DESCRIPTION

Figure 1:
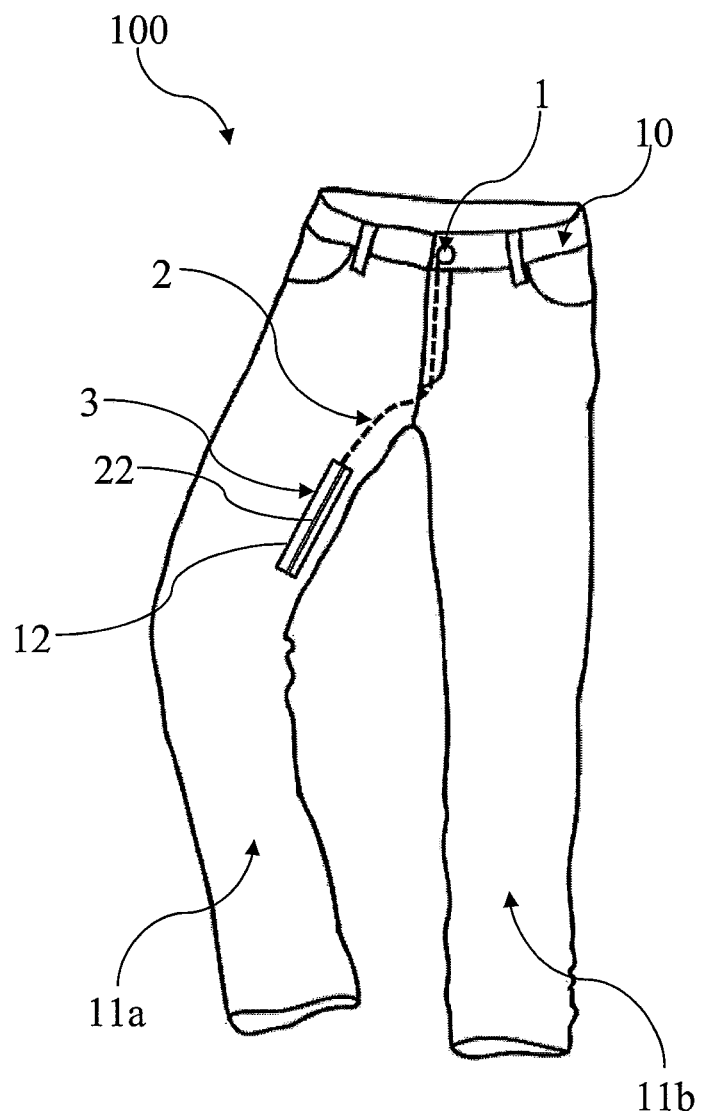
FIG. 1 shows schematically a perspective view of a wearable step counter system according to an embodiment of the present invention.

FIG. 1 shows a wearable step counter system 100 according an embodiment of the present invention. The step counter system 100 comprises a garment 10 for a wearer's legs, a capacitive electrode 3 and a microcontroller 1.

The garment 10 shown in FIG. 1 is a two-legged garment, for example a pair of pants, comprising a first garment leg 11a and a second garment leg 11b.

The capacitive electrode 3 comprises an electrically conductive yarn 22 woven in a textile fabric portion 12 of the garment 10. Some embodiments of the present invention provide that the garment 10 comprises a textile fabric portion 12 that forms part of one of the two garment legs 11a, 11b itself. In the embodiment shown in FIG. 1 the textile fabric portion 12 is arranged on the first garment leg 11a. In general the textile fabric portion 12 forms part of the garment 10 for providing a parasitic capacitive coupling between the capacitive electrode 3 and a wearer's leg.

In other words, the textile fabric portion 12 of the garment 10, on which the electrically conductive yarn 22 of the capacitive electrode 3 is woven, is configured to at least partially cover a wearer's leg. Thus, the textile fabric portion 12 is arranged on the garment 10, at a position such that the capacitive electrode 3 faces towards the wearer's other leg. In the embodiment shown in FIG. 1 the capacitive electrode 3 is arranged on a region of the garment 10 between the wearer's legs, i.e. a region configured to be located between the wearer's legs when the garment 10 is worn by the user. Some embodiments of the present invention provide that the textile fabric portion 12 is arranged on the garment 10 at a region configured to be placed at the inner thigh of the wearer, but the textile fabric portion 12 containing the electrically conductive yarn 22 may be disposed at various other locations in various other embodiments.

The microcontroller 1 is electrically connected to the capacitive electrode 3 (e.g. by means of a connection cable 2 shown in dotted line) for evaluating the parasitic capacitive coupling between the capacitive electrode 3 and the leg of the wearer within second garment leg 11b, i.e. the leg of the wearer opposite to the leg covered at least partially by the textile fabric portion 12 on which the electrically conductive yarn 22 is woven. Connection cable 2 advantageously extends along a seam in the garment 10 in various embodiments. Connection cable 2 advantageously electrically connects microcontroller 1 to fabric portion 12 of the capacitive electrode 3 in some embodiments.

In this way, when the wearer is walking, the capacitive electrode 3 follows a leg of the wearer and is moved with respect to the other leg. This movement influences the parasitic capacitive coupling between the capacitive electrode 3 and the leg of the wearer within second garment leg 11b. Thus, by sensing the parasitic capacitive coupling, the movement between the wearer's legs can be detected by the microcontroller 1. In particular, the parasitic capacitive coupling can be evaluated by detecting a capacitance value C of the capacitive electrode 3.

In fact, when the leg of the wearer (or in general any other capacitance provided object) is moved towards the capacitive electrode 3, the value C of the capacitance is changed because the parasitic capacitance of the wearer's leg $C_{LEG}$ is added to the value C leading to new value of the global capacitance sensed by the microcontroller 1. The capacitance value C increases with decreasing distance and with increased cross-sectional overlap, between the capacitive electrode 3 and the wearer's leg within second garment leg 11b.

The microcontroller 1 can be housed for example into an electronic button being electrically connected to the capacitive electrode 3 by an input stage circuit (not shown) as described in the European patent application No. 15179147.2 in the name of the same Applicant and having the following title: "Electronic button for smart garments" (see in particular page 15, lines 5-20), the contents of which are incorporated herein by reference as if set forth in their entirety. In some embodiments of the present invention the microcontroller 1 detects the capacitance value C of the capacitive electrode 3 by measuring a time delay due to a changing of the charging/discharging time of the capacitive electrode 3 due in turn to a changing of the capacitance value C of the capacitive electrode 3.

Figure 2A:
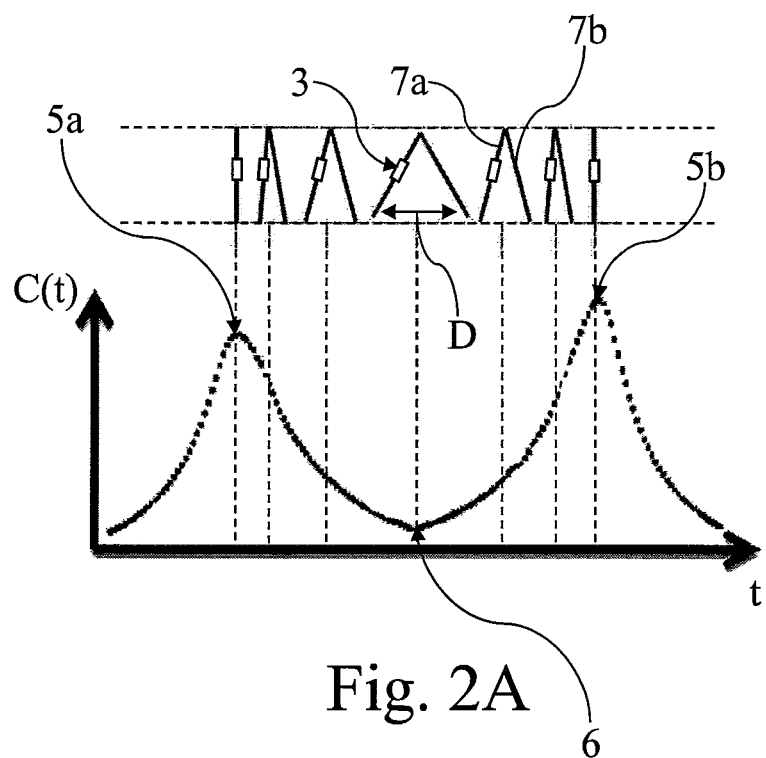
FIG. 2A is a time graph of the capacitive values of a capacitive electrode detected by a wearable step counter system according to an embodiment of the present invention.

The microcontroller 1 is advantageously configured to evaluate the capacitance value C of the capacitive electrode 3 as a function of time, for example the detected capacitance values C being acquired in the form of a sampled signal C(t) over time as shown in FIG. 2A. In particular, the capacitance value C provides values which increase with decreasing distance between the wearer's legs and which increase with increasing cross-sectional overlap, between the capacitive electrode 3 and the wearer's leg within second garment leg 11b.

Figure 2B:
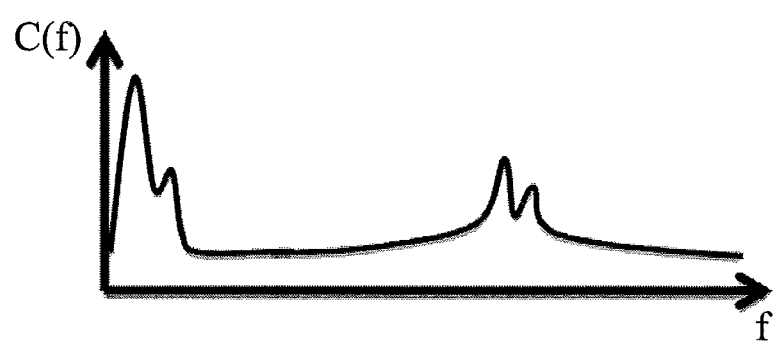
FIG. 2B is a frequency spectrum of the capacitive values of a capacitive electrode detected by a wearable step counter system according to an embodiment of the present invention.
Figure 2C:
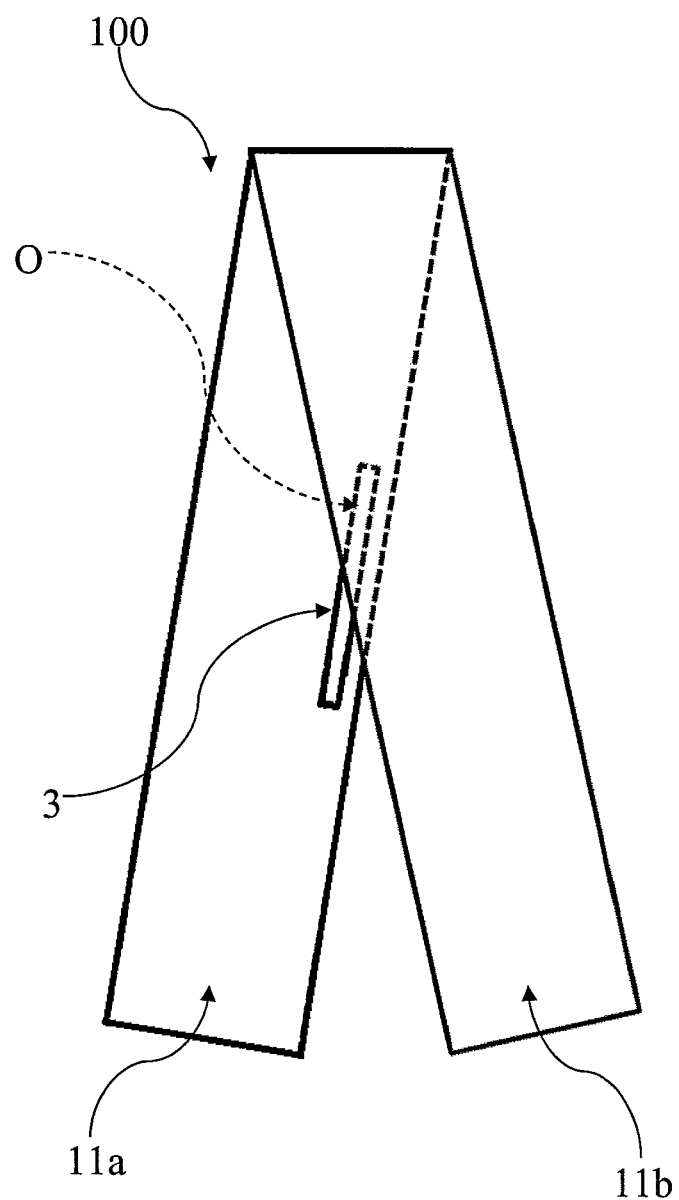
FIG. 2C shows schematically a perspective lateral view of a wearable step counter system according to an embodiment of the present invention.

As shown in FIG. 2C, the amount of cross-sectional overlap O between the capacitive electrode 3 and the wearer's leg within second garment leg 11b, depends upon the position of the wearer's leg within first garment leg 11a and thus the capacitive electrode 3, with respect to the wearer's leg within second garment leg 11b.

In FIG. 2A the capacitance values C provide two peaks 5a, 5b representing a step carried out by the wearer. The wearer's legs are indicated in FIG. 2A symbolically by two segments 7a, 7b (the capacitive electrode 3 is symbolically arranged on the leg represented by the segment 7a). In other words, the time interval between two peaks 5a, 5b is indicative of the time during which a step is carried out by the wearer. In this way the microcontroller 1 detects and counts the steps carried out by the wearer during a physical activity. Moreover, the microcontroller 1 is configured to evaluate the distance D between the wearer's legs on the basis of the parasitic capacitive coupling. For example, the distance D can be defined by the angle formed between the wearer's legs, or by the average distance between a predetermined point on the wearer's leg on which the capacitive electrode 3 is located, and the other leg. For example the distance D can be calculated by multiplying the inverse of the capacitance value C with a conversion coefficient K (D=K*1/C), wherein K is a coefficient experimentally derived from previous tests. Some embodiments of the present invention provide that the distance D between the wearer's legs is evaluated from the capacitance value C provided at the valley 6 between the two peaks 5a, 5b. In this way, the distance D is indicative of the distance carried out by the user during the step (i.e. during the time interval between the two peaks 5a, 5b). Other methods may be used for determining distance D, in other embodiments.

FIG. 2B shows the frequency spectrum C(f) of the sampled signal C(t) shown in FIG. 2A. In particular, an embodiment of the step counter system according to the invention provides that the microcontroller is configured to evaluate the Fourier transform of the time domain detected capacitance signal C(t) to differentiate different walking styles. For example, the microcontroller can calculate the Fourier transform by using a Fast Fourier Transform (FFT) algorithm. The calculated frequency spectrum C(f) is then compared with a plurality of frequency spectrum stored in a memory associated to a plurality of walking styles experimentally derived from previous tests. On the basis of this comparison, the microcontroller 1 detects the walking style of the wearer. The conversion coefficient K is chosen for example from a plurality of values. For each walking style stored, a conversion coefficient value is associated, so that the distance walked by the wearer can be determined with high accuracy.

Figure 3:
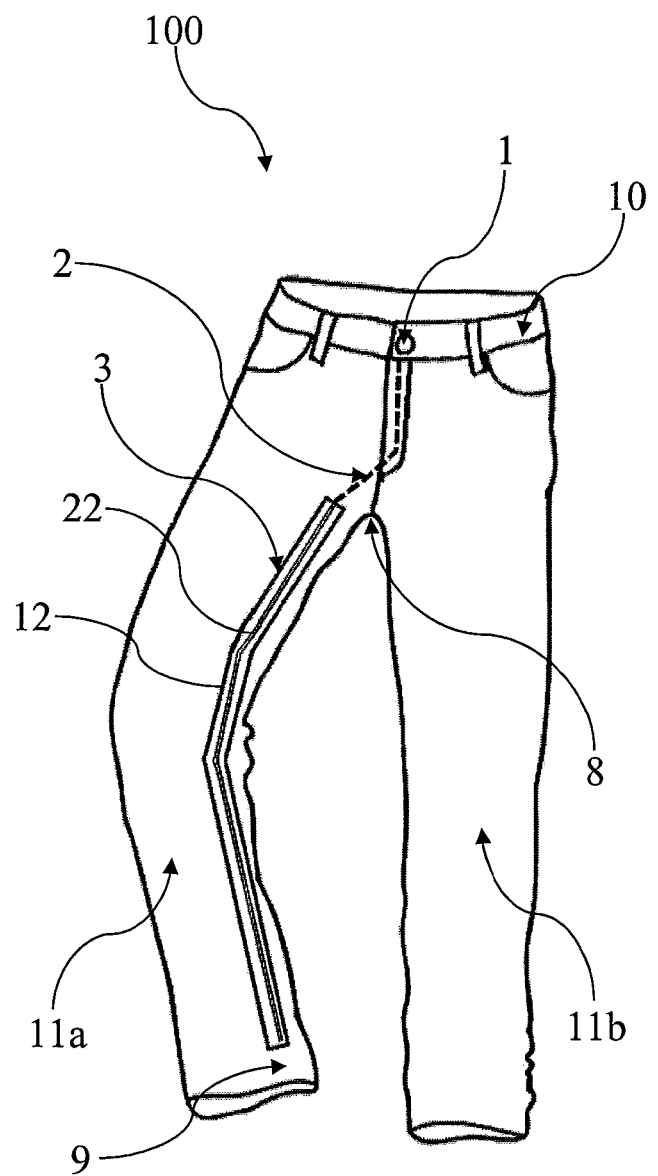
FIG. 3 shows schematically a perspective view of a wearable step counter system according to a further embodiment of the present invention.

FIG. 3 shows an embodiment of the present invention wherein the capacitive electrode 3 is arranged substantially along the full length of the garment 10. The term "substantially along the full length of the garment" or "substantially along the entire length of the garment" is used to signify that the capacitive electrode 3 is arranged on the garment and extends fully along and completely occupies a region having a length greater than a half of the main length of the garment.

In the embodiment shown in FIG. 3, the garment is a pair of pants, thus the main length is the inner length of a garment leg 11a, 11b. In this case, the textile fabric portion 12 is arranged along a path connecting the pants crotch 8 with the pants ankle 9.

The Applicant observed that the step counter system 100 with a capacitive electrode 3 arranged substantially along the full length of the garment 10 enables an improvement in the accuracy of the walking style detection. This improvement is especially noted in step counter systems 100 wherein the garment 10 comprises garment leg/s having a length arranged to cover the full or almost full leg/s of the wearer, e.g. from the crotch to the ankle as shown in the embodiment of FIG. 3.

Some embodiments of the present invention provide that, in the case of a step counter system 100 wherein the garment is a pair of pants, the electrically conductive yarn 22 of the capacitive electrode 3 is woven into a textile fabric portion 12 arranged along the seam such as along the inner thigh of the pants. In this way, the capacitive electrode 3 can be assembled onto the garment 10 without losing physical comfort and stylish appearance.

In some embodiments of the present invention, the textile fabric portion 12 can be realized substantially as described in the European patent application No. 15193723.2 in the name of the same Applicant and having the following title: "A textile fabric implementing a capacitive grid" (see in particular from page 5, line 13 to page 8, line 30), the contents of which is incorporated herein by reference as if set forth in its entirety.

Figure 4:
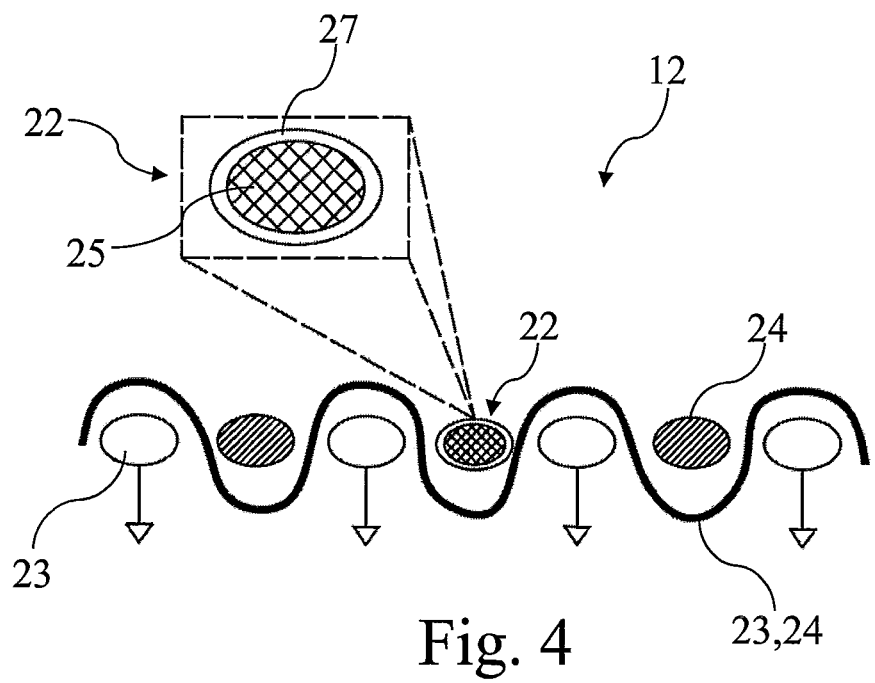
FIG. 4 shows schematically a cross-sectional view of a textile fabric portion of a wearable step counter system according to an embodiment of the present invention.

In particular, FIG. 4 shows a textile fabric portion 12 according to an embodiment of the invention comprising a non-isolated set, i.e. group of conductive yarns 23 interlaced with the electrically conductive yarn 22.

In some embodiments the electrically conductive yarn 22 and the non-isolated set, i.e. group, of conductive yarns 23 are interlaced by a plurality of interlacing textile yarns, wherein some of the interlacing textile yarns are non-isolated conductive yarns 23 in order to form an electrical grounding grid with the conductive yarns 23 of the non-isolated set of conductive yarns 23.

Moreover, part of the interlacing textile yarns is conventional isolating textile yarns 24. Therefore, the interlacing textile yarns comprise both isolating and non-isolating yarns. In this manner, an electrical grounding grid is formed.

In the embodiment of FIG. 4, the electrically conductive yarn 22 and the non-isolated set of conductive yarns 23 are warp yarns and the interlacing textile yarns 23, 24 are weft yarns.

Nevertheless, in an alternative embodiment, the electrically conductive yarn 22 and the non-isolated set of conductive yarns 23 may be weft yarns and the interlacing textile yarns 23, 24 may be warp yarns.

In the textile fabric portion of FIG. 4, the electrically conductive yarn 22, the isolating textile yarns 24 and the non-isolated set of conductive yarns 23 form a single textile layer.

Some embodiments of the present invention provide that the electrically conductive yarn 22 is externally isolated. For example, the electrically conductive, externally isolated yarn 22 is core spun with a conductive center 25 and an isolating external surface 27. The isolating external surface 27 can be made for example of an isolating resin and/or isolating fibers.

The conductive core 25 of the electrically conductive, externally isolated yarn 22 can be made for example of a material such as steel, copper, silver, a conductive polymer or various combinations thereof. In further embodiments, the conductive core 25 may be a magnet wire or enameled wire, i.e. a metallic wire (typically made of copper or aluminum) coated with a very thin layer of insulation.

The isolating external surface 27 of the electrically conductive, externally isolated yarn 22 can be made for example of a material such as cotton, polyester, polyurethane, polypropylene, or various combinations thereof.

In some embodiments, the non-isolated conductive yarns 23 are made of steel or of steel twisted around cotton or of a steel-cotton blend.

Finally, the isolating yarns 24 can be made for example of a textile material such as cotton, polyester, nylon, various functional derivatives thereof or various combinations thereof.

Figure 5:
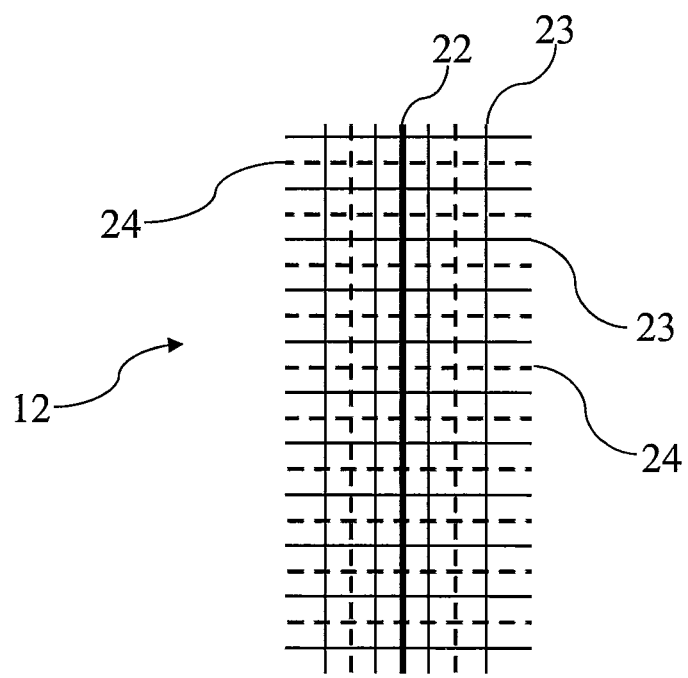
FIG. 5 shows schematically a top view of the textile fabric portion of shown in FIG. 4.

FIG. 5 shows a top view of the textile fabric portion of FIG. 4, wherein the non-isolated conductive yarns 23 form a dense sequence of contacting yarns, electrically connected to an electrical ground reference to provide an electrical grounding grid.

Figure 6:
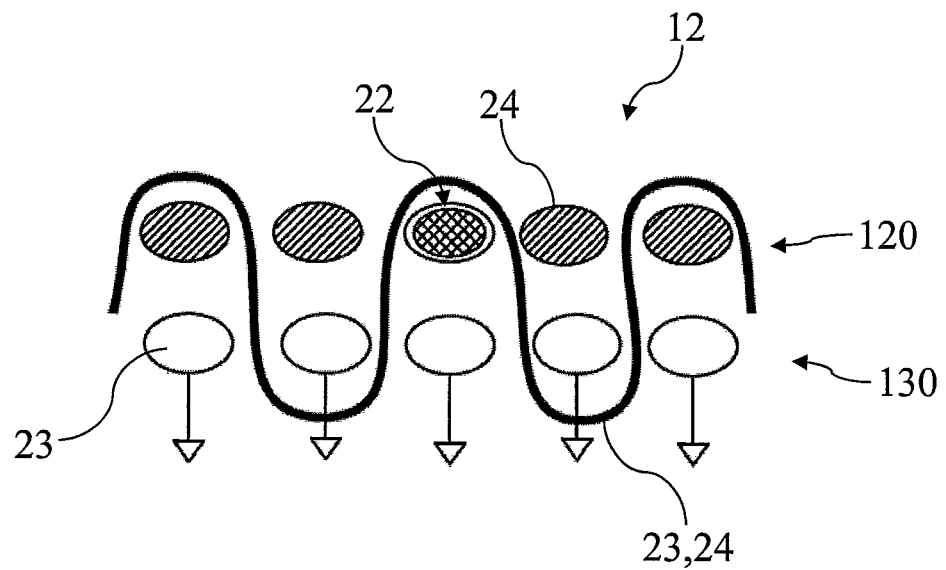
FIG. 6 shows schematically a cross-sectional view of a textile fabric portion of a wearable step counter system according to a further embodiment of the present invention.

With reference to FIG. 6, a further embodiment of the invention provides that the electrically conductive yarn 22 and the isolating yarns 24 form a first textile layer 120, and the non-isolated set of conductive yarns 23 form a second textile layer 130 superimposed on the first textile layer 120.

In this embodiment, the first and the second textile layer 120, 130 are woven together by interlacing textile yarns. In particular, part of the interlacing textile yarns are non-isolated conductive yarns 23 in order to form an electrical grounding grid with the non-isolated conductive yarns 23 of the non-isolated set of yarns of the second textile layer 130 and part of the interlacing textile yarns are isolating textile yarns 24.

Also for this embodiment, the electrically conductive yarn 22 and the non-isolated set of yarns 23 may be warp yarns and the interlacing textile yarns 23, 24 may be weft yarns.

In an alternative embodiment, the electrically conductive yarn 22 and the non-isolated set of yarns 23 may be weft yarns and the interlacing textile yarns 23, 24 may be warp yarns.

Figure 7:
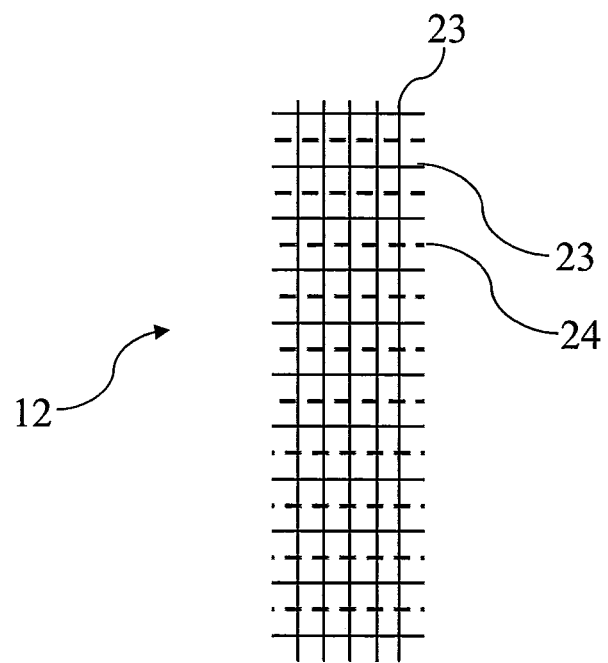
FIG. 7 shows schematically a bottom view of the textile fabric portion 12 of FIG. 6.

In FIG. 7 a bottom view of the textile fabric portion 12 of FIG. 6 is represented in order to show the electric grounding grid formed by warp non-isolated conductive yarns 23 interlacing with weft non-isolated conductive yarns 23.

Figure 8:
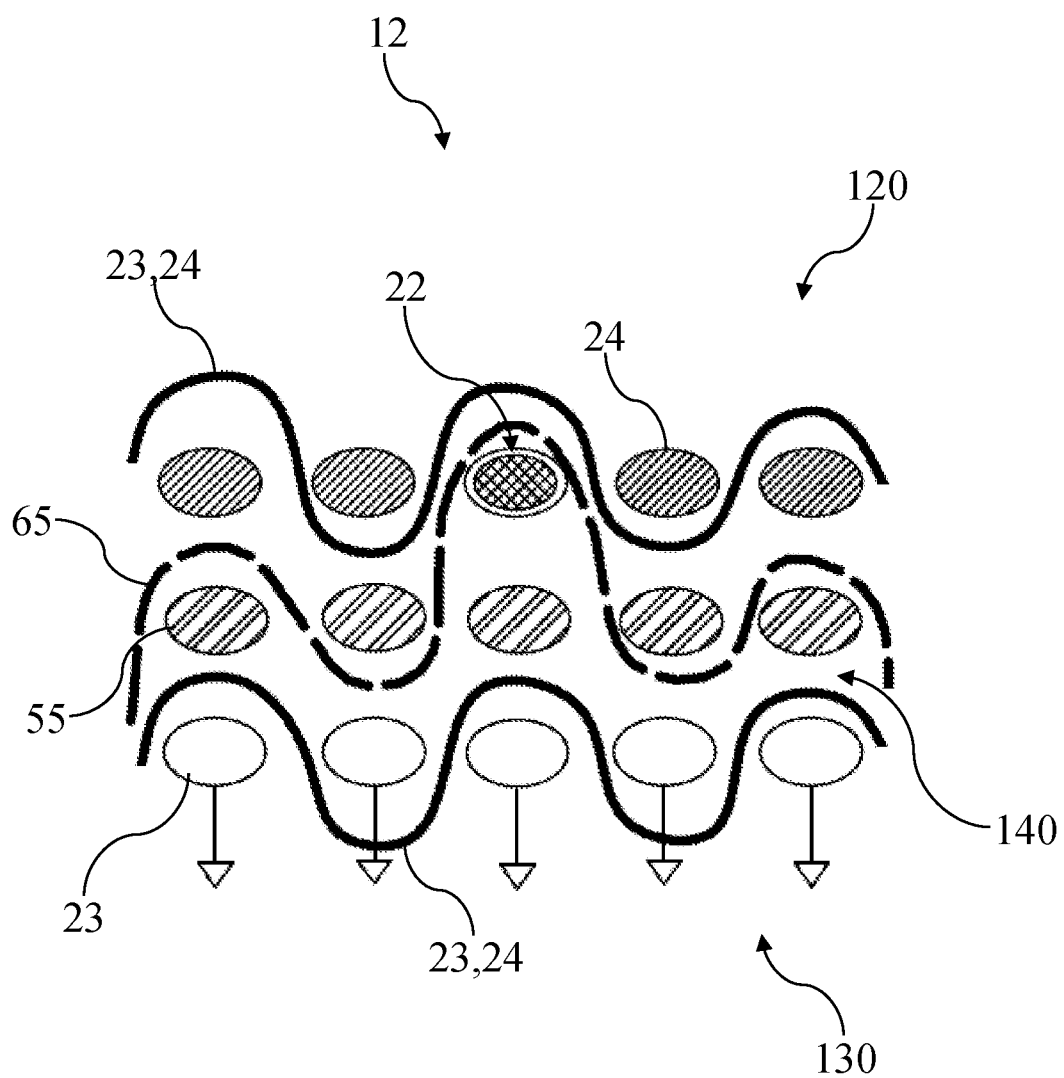
FIG. 8 schematically a cross-sectional view of a textile fabric portion of a wearable step counter system according to a further embodiment of the present invention.

FIG. 8 shows a further embodiment of the textile fabric portion 12 according to the invention. In this embodiment, the electrically conductive yarn 22 and the isolating yarns 24 form a first textile layer 120, and the non-isolated set of yarns 23 form a second textile layer 130.

The textile fabric portion 12 of FIG. 8 further comprises a further set of structural isolating yarns 55 forming an intermediate textile layer 140 interposed between the first and second textile layers 120, 130.

Moreover, the textile fabric portion 12 of FIG. 8 further comprises a plurality of structural isolating yarns 65 interlacing the first and second textile layer and the third intermediate layer 140 of structural yarns 55.

The intermediate textile layer 140 is an actual textile layer, made of ordinary textile yarns 55, 65, such as cotton, polyester or the like and mechanically woven together as any ordinary textile according to various embodiments.

In the embodiment of FIG. 8, the second textile layer 130 is woven together by interlacing textile yarns, wherein part of the interlacing textile yarns are non-isolated conductive yarns 23 in order to form an electrical grounding grid with the non-isolated conductive yarns 23 of the non-isolated set of yarns of the second textile layer 130 and part of the interlacing textile yarns are isolating textile yarns 24.

In any case, also for the embodiment of FIG. 8, the electrically conductive yarn 22 and the non-isolated set of yarns 23 may be warp yarns and the interlacing yarns may be weft yarns. Nevertheless, in an alternative embodiment, the electrically conductive yarn 22 and the non-isolated set of yarns 23 may be weft yarns and the interlacing yarns may be warp yarns.

Figure 9:
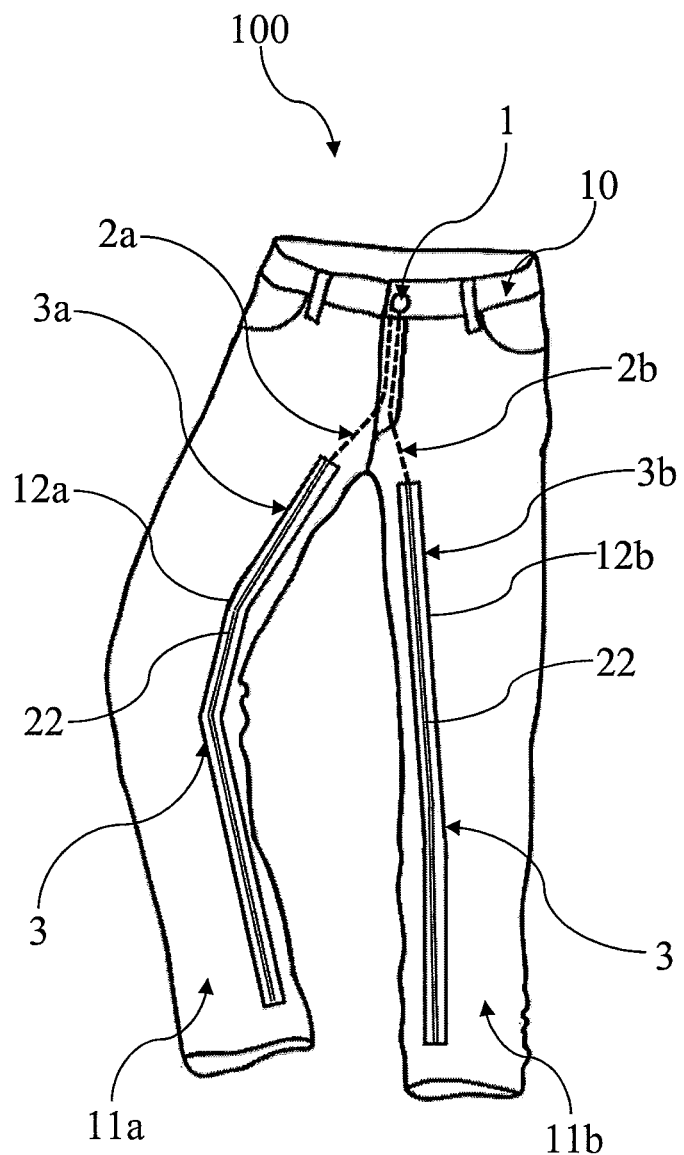
FIGS. 9, 10 and 11 show further embodiments of the wearable step counter system according to the present invention.

In FIG. 9 a further embodiment of the step counter system 100 according the present invention is shown. In this embodiment the textile fabric portion 12 comprises a first textile fabric portion 12a arranged on the first garment leg 11a and a second textile fabric portion 12b arranged on the second garment leg 11b.

The step counter system 100 of FIG. 9 comprises two capacitive electrodes 3, wherein each capacitive electrode is arranged on a garment leg. In particular, a first capacitive electrode 3a has an electrically conductive yarn 22 woven into the first textile fabric portion 12a, a second capacitive electrode 3b has an electrically conductive yarn 22 woven into said second textile fabric portion 12b. In other words, the step counter system 100 of FIG. 9 has the capacitive sensing structure shown in the embodiment of FIG. 3 in both garment legs 11a, 11b. The embodiment of FIG. 9 comprises two capacitive electrodes 3a, 3b arranged on the garment legs 11a, 11b, respectively, and substantially along the full length of the garment 10. In further embodiments, the invention provides a step counter system 100 comprising two capacitive electrodes 3a, 3b having different lengths with respect to each other and/or arranged in different positions on the garment legs 11a, 11b.

As schematically shown in FIG. 9, the first and the second capacitive electrodes 3a, 3b are electrically connected to the microcontroller 1, e.g. by means of connection cables 2a and 2b respectively (shown in dotted line).

In this embodiment, the microcontroller is configured to detect the capacitive value C of each capacitive electrode 3a, 3b. In this way the detected capacitance values C is acquired in the form of two sampled signals C(t) over time as shown in FIG. 2A. Some embodiments of the present invention provide that the microcontroller 1, by summing the detected capacitive values C of each capacitive electrode 3a, 3b, provides a time domain detected capacitance signal C(t) with a detection sensitivity improved.

Figure 10:
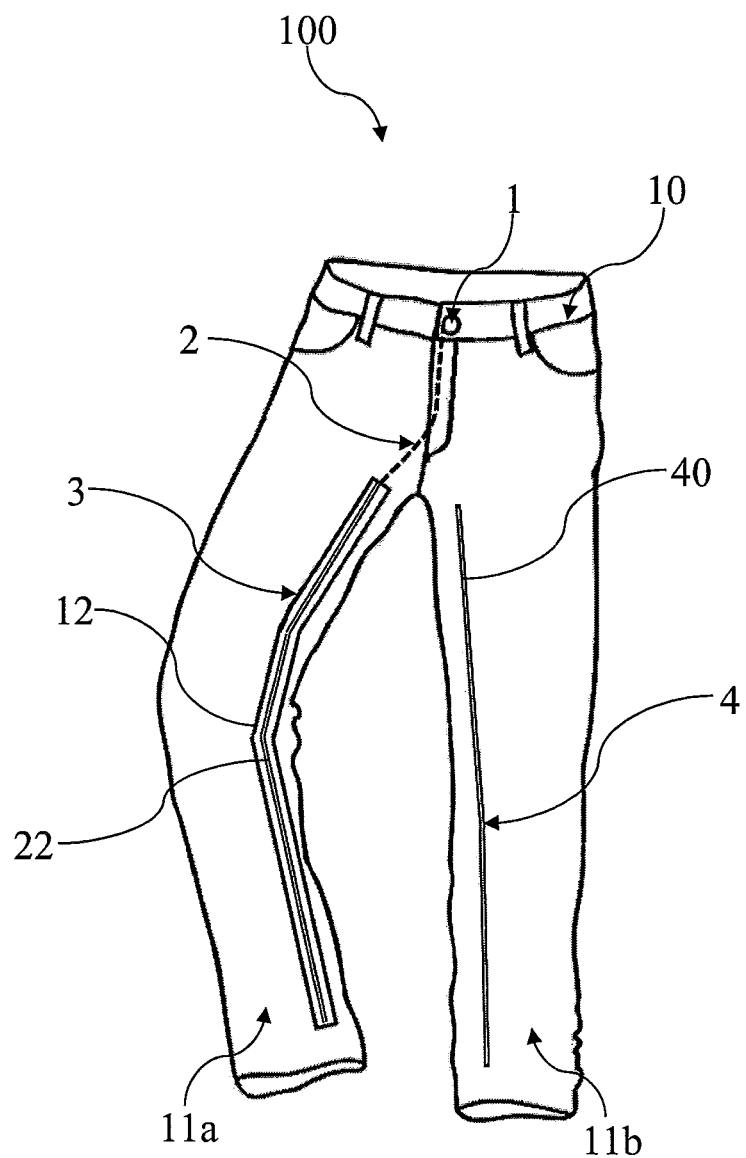

FIG. 10 shows a further embodiment of the present invention. In this embodiment the wearable step counter system 100 comprises a matching electrode 4 arranged on the second garment leg 11b and extending substantially along the full length of the garment 10. The matching electrode 4 comprises an electrically conductive yarn 40. The matching electrode 4 provides for enhanced sensibility of the parasitic capacitive coupling detection in response to a relative movement of the wearer's legs in a similar manner to the embodiment of FIG. 9. The parasitic capacitance coupling between the capacitive electrode 3 (arranged on the garment leg 11a) and the matching electrode 4 (arranged on the second garment leg 11b) provides an accurate and precise dynamic capacitance profile as a function of time. In some embodiments, the electrically conductive yarn 40 is an isolated conductive yarn, for example made as the electrically conductive yarn 22 which comprises an electrically conductive core 25 and an electrically insulating external surface 27. In some embodiments, the conductive yarn 40 is connected to ground, so that the capacitive electrode 3 works as a sensing electrode and the matching electrode 4 working as a reference to the capacitive electrode 3. In this way the microcontroller detects the capacitance value of the capacitive electrode 3 with respect to the ground.

Figure 11:
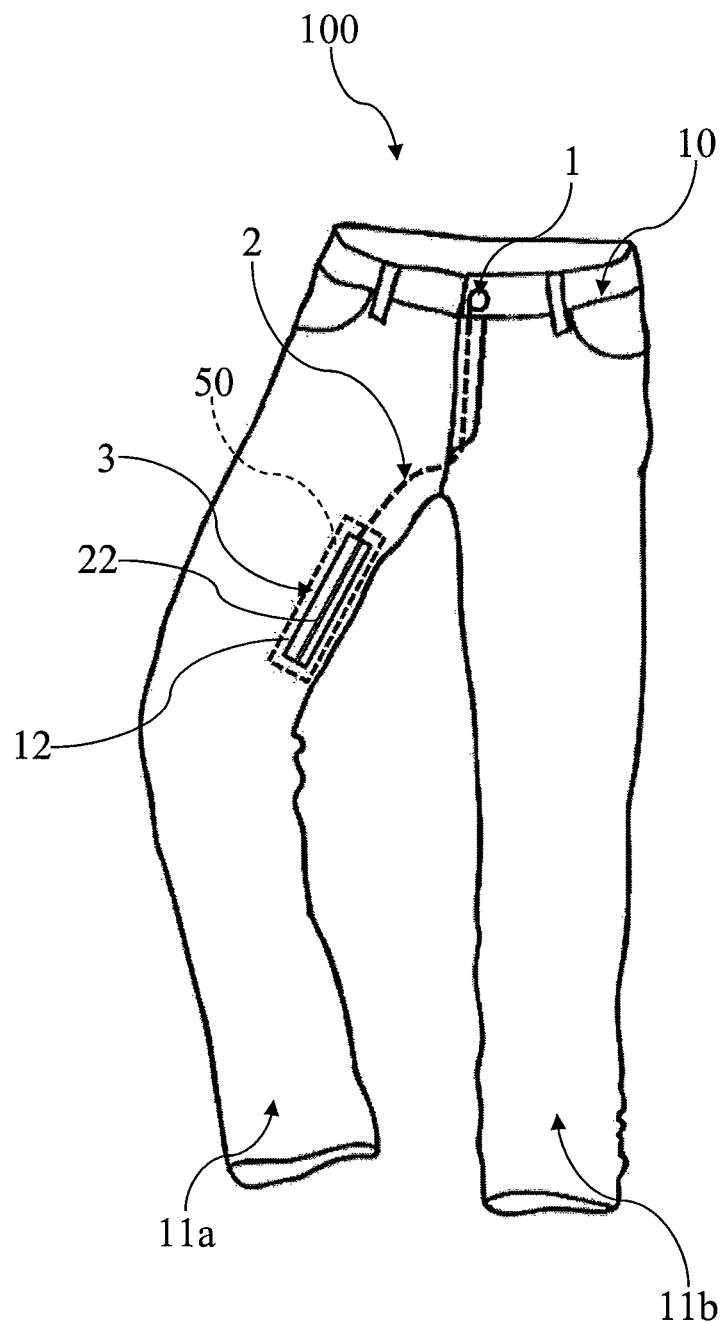

FIG. 11 illustrates another embodiment of the disclosure. In the embodiment of FIG. 11, the capacitive electrode 3 includes a coating 50 that serves as a capacitive sensor. FIG. 11 shows coating 50 on first garment leg 11a.

Electrically conductive yarn 22 woven into textile fabric portion 12 of garment 10, works in conjunction with coating 50 according to this embodiment. In this embodiment the coating may be a flexible (co)polymer matrix with dispersed conductive impurities formed using a variety of different materials. Various suitable conductive impurities may be used and various types of suitable conductive coatings may be used in various embodiments. According to this embodiment, coating 50 is a conductive coating that functions as the capacitive sensor and the electrically conductive yarn 22 functions as a shield or ground scheme. Coating 50 may be formed on the inside or outside of the garment fabric. In some embodiments, connection cable 2 shown in dotted line advantageously extends along a seam of the garment and electrically connects microcontroller 1 to coating 50 of the capacitive electrode 3 in some embodiments.

Summarizing, the present invention relates to a wearable step counter system 100 comprising a garment 10 for a wearer's legs, a capacitive electrode 3 and a microcontroller 1, the garment 10 comprising a textile fabric portion 12, the capacitive electrode 3 comprising an electrically conductive yarn 22 woven into the textile fabric portion 12, the textile fabric portion 12 being disposed on or in or forming part of the garment 10 for providing a parasitic capacitive coupling between the capacitive electrode 3 and a wearer's leg, the microcontroller 1 being electrically connected to said capacitive electrode 3 for evaluating parasitic capacitive coupling so that the relative movement between the wearer's legs is detected by the microcontroller 1.

In some embodiments, the microcontroller 1 is configured to evaluate the parasitic capacitive coupling by detecting a capacitance value C of the capacitive electrode 3.

In some embodiments, the microcontroller is electrically connected to the capacitive electrode by a wire that extends along a seam of the garment.

In some embodiments, the textile fabric portion comprising the electrically conductive yarn, is disposed along a seam of the garment.

In some embodiments, the microcontroller is configured to evaluate a distance between the wearer's legs based on the parasitic capacitive coupling.

In some embodiments, the microcontroller 1 is configured to evaluate at least one of distance D between the wearer's legs and a cross-sectional overlap O of the capacitive electrode and the wearer's leg, on the basis of the parasitic capacitive coupling.

In some embodiments, the microcontroller is configured to evaluate a value of a parasitic capacitance associated with the parasitic capacitive coupling, as a function of time.

In some embodiments, the capacitive electrode extends substantially or completely along the full length of the garment.

In some embodiments, the microcontroller detects parasitic capacitance associated with the parasitic capacitive coupling, at multiple locations along the full length of the garment.

In some embodiments, the electrically conductive yarn includes an electrically conductive core and an electrically insulating external surface.

In some embodiments, the electrically conductive core is made of at least one of steel, copper, silver and a conductive polymer.

In some embodiments, the electrically insulating external surface is made of cotton, polyester, polyurethane or polypropylene.

In some embodiments, the textile fabric portion comprises a plurality of non-isolated conductive yarns interlaced with the electrically conductive yarn, the plurality of non-isolated conductive yarns adapted to provide an electrical grounding grid that touches the wearer's skin.

In some embodiments, the non-isolated conductive yarns are made of steel, steel twisted around cotton or a steel-cotton blend.

In some embodiments, the garment is a two-legged garment with a first garment leg and a second garment leg, wherein the textile fabric portion 12 comprises a first textile fabric portion 12a of the first garment leg 11a and a second textile fabric portion 12b of the second garment leg 11b, the capacitive electrode comprising first 3a and second 3b capacitive electrodes 3, the electrically conductive yarn 22 of the first capacitive electrode 3a being woven into the first textile fabric portion 12a, the electrically conductive yarn 22 of the second capacitive electrode 3b being woven into the second textile fabric portion 12b.

In some embodiments, the garment is a two-legged garment comprising a first garment leg and a second garment leg, the textile fabric portion 12 comprises a first textile fabric portion 12a of the first garment leg 11a, and further comprising a matching electrode 4 disposed on or in or forming at least part of the second garment leg 11b, the matching electrode 4 comprising an electrically conductive yarn 40 connected to ground.

In some embodiments, the matching electrode 4 is arranged substantially along the full length of the garment 10 the garment 10 is a pair of pants.

In some embodiments, the wearable step counter system comprises a garment for a wearer's legs, a capacitive electrode and a microcontroller, the garment including a textile fabric portion with electrically conductive yarn woven into the textile fabric portion and forming part of the garment, the electrically conductive yarn being electrically grounded and the textile fabric portion further comprising a conductive coating disposed thereon and forming the capacitive electrode adapted for providing a parasitic capacitive coupling between the capacitive electrode and a wearer's leg, the microcontroller being electrically connected to the capacitive electrode for evaluating the parasitic capacitive coupling to detect relative movement between the wearer's legs.

In some embodiments, the conductive coating comprises a flexible copolymer matrix with dispersed conductive impurities therein.

The method for detecting a number of steps of a user comprises the main steps of:
i. providing a garment for a wearer's legs, the garment including a capacitive electrode and a microcontroller coupled thereto, the garment including a textile fabric portion with electrically conductive yarn woven into the textile fabric portion and forming part of a first leg of the garment, the electrically conductive yarn forming the capacitive electrode, and
ii. detecting parasitic capacitance between the capacitive electrode and the second leg of the garment.

In some embodiments, the detecting comprises detecting the parasitic capacitance at a plurality of locations along the second leg.

In some embodiments, the method further comprising converting the parasitic capacitance to distance between the capacitive electrode on the first leg, and the wearer's leg disposed in the second leg of the garment.

In some embodiments, the detecting comprises detecting at least periodically over a period of time, and further comprising calculating a number of steps taken by wearer based on the detecting at least periodically over a period of time.

The wearable step counter system according to the present invention can be produced by means of a method comprising the steps of:
a) providing a garment 10 for a wearer's legs, the garment 10 having a textile fabric portion 22;
b) weaving an electrically conductive yarn 22 into the textile fabric portion 12 for providing a capacitive electrode 3;
c) providing a microcontroller 1 electrically connected to the capacitive electrode 3 for evaluating the parasitic capacitive coupling between the capacitive electrode 3 and a wearer's leg, so that the relative movement between the wearer's legs is detected by the microcontroller 1.

The invention claimed is:

1. A wearable step counter system comprising a garment for a wearer's legs, a capacitive electrode and a microcontroller,
said garment comprising a first garment leg, a second garment leg and a textile fabric portion, said capacitive electrode comprising a single electrically conductive yarn woven into said textile fabric portion, said textile fabric portion being disposed on or in or forming part of said first garment leg for providing a parasitic capacitive coupling between said single capacitive electrode and a parasitic capacity of said second garment leg, said microcontroller being electrically connected to said single capacitive electrode for evaluating said parasitic capacitive coupling so that relative movement between the first garment leg and the second garment leg is detected by the microcontroller.

2. The wearable step counter system according to claim 1, wherein said microcontroller is configured to evaluate said parasitic capacitive coupling by detecting a capacitance value of said capacitive electrode.

3. The wearable step counter system according to claim 1, wherein said microcontroller is electrically connected to said capacitive electrode by a wire that extends along a seam of said garment.

4. The wearable step counter system according to claim 1, wherein said textile fabric portion comprising said electrically conductive yarn, is disposed along a seam of said garment.

5. The wearable step counter system according to claim 1, wherein said microcontroller is configured to evaluate a distance between the first garment leg and the second garment leg based on said parasitic capacitive coupling.

6. The wearable step counter system according to claim 1, wherein the microcontroller is configured to evaluate at least one of a distance between the first garment leg and the second garment leg and a cross-sectional overlap of the capacitive electrode and the second garment leg, based on said parasitic capacitive coupling.

7. The wearable step counter system according to claim 1, wherein said microcontroller is configured to evaluate a value of a parasitic capacitance associated with said parasitic capacitive coupling, as a function of time.

8. The wearable step counter system according to claim 1, wherein said capacitive electrode extends substantially along a full length of said garment.

9. The wearable step counter system according to claim 8, wherein said microcontroller detects parasitic capacitance associated with said parasitic capacitive coupling, at multiple locations along the full length of said garment.

10. The wearable step counter system according to claim 1, wherein said electrically conductive yarn includes an electrically conductive core and an electrically insulating external surface.

11. The wearable step counter system according to claim 10, wherein said electrically conductive core is made of at least one of steel, copper, silver and a conductive polymer.

12. The wearable step counter system according to claim 10, wherein said electrically insulating external surface is made of cotton, polyester, polyurethane or polypropylene.

13. The wearable step counter system according to claim 1, wherein said textile fabric portion comprises a plurality of non-isolated conductive yarns interlaced with said electrically conductive yarn, said plurality of non-isolated conductive yarns adapted to provide an electrical grounding grid that touches the wearer's skin.

14. The wearable step counter system according to claim 13, wherein said non-isolated conductive yarns are made of steel, steel twisted around cotton or a steel-cotton blend.

15. The wearable step counter system according to claim 1, wherein said garment is a two-legged garment with said first garment leg and second garment leg, wherein said textile fabric portion comprises a first textile fabric portion of said first garment leg and a second textile fabric portion of said second garment leg, said capacitive electrode comprising first and second capacitive electrodes, the electrically conductive yarn of the first capacitive electrode being woven into said first textile fabric portion, the electrically conductive yarn of the second capacitive electrode being woven into said second textile fabric portion.

16. The wearable step counter system according to claim 1, wherein said garment is a two-legged garment comprising said first garment leg and said second garment leg, said textile fabric portion comprises a first textile fabric portion of said first garment leg, and further comprising a matching electrode disposed on or in or forming at least part of said second garment leg, said matching electrode comprising an electrically conductive yarn connected to ground.

17. The wearable step counter system according to claim 16, wherein said matching electrode is arranged substantially along a full length of said garment and said garment is a pair of pants.

18. A wearable step counter system comprising a garment for a wearer's legs, a capacitive electrode and a microcontroller, said garment including a textile fabric portion with electrically conductive yarn woven into said textile fabric portion and forming part of said garment, said electrically conductive yarn being electrically grounded and said textile fabric portion further comprising a conductive coating disposed thereon and forming said capacitive electrode adapted for providing a parasitic capacitive coupling between said capacitive electrode and a garment leg, said microcontroller being electrically connected to said capacitive electrode for evaluating said parasitic capacitive coupling to detect relative movement between a first leg and a second leg of said garment.

19. The wearable step counter system according to claim 18, wherein said conductive coating comprises a flexible copolymer matrix with dispersed conductive impurities therein.

20. A method for detecting a number of steps of a wearer, said method comprising:
providing a first leg of a garment, said garment including a capacitive electrode and a microcontroller coupled to said capacitive electrode, said garment including a textile fabric portion with a single electrically conductive yarn woven into said textile fabric portion and forming part of said first leg of said garment, said single electrically conductive yarn forming said capacitive electrode, and
detecting capacitance between said capacitive electrode and a parasitic capacitance of a second leg of said garment.

21. The method as in claim 20, wherein said detecting comprises detecting said parasitic capacitance at a plurality of locations along said second leg of said garment.

22. The method as in claim 20, further comprising converting said parasitic capacitance to a distance between said capacitive electrode on said first leg of said garment and said second leg of said garment.

23. The method as in claim 22, wherein said detecting comprises detecting over a period of time, and further comprising calculating a number of steps taken by the wearer based on said detecting over said period of time.

24. A method for producing a wearable step counter system comprising the steps of:
providing a garment for a wearer's legs, said garment having a textile fabric portion;
weaving an electrically conductive yarn into said textile fabric portion for providing a capacitive electrode in a first garment leg; and
providing a microcontroller electrically connected to said capacitive electrode for evaluating a parasitic capacitive coupling between said capacitive electrode and a parasitic capacitive of a second garment leg, so that the relative movement between the wearer's legs is detected by the microcontroller.

25. The method according to claim 24, wherein said electrically conductive yarn is woven into said textile fabric during production of said textile fabric and wherein said providing the garment includes tailoring said textile fabric into a garment.

* * * * *